United States Patent [19]

Drake et al.

[11] Patent Number: 5,270,424
[45] Date of Patent: Dec. 14, 1993

[54] HYDROSILYLATION PROCESS

[75] Inventors: Robert A. Drake, Penarth; Brian J. Griffiths, Coytrahen; David R. Thomas, Barry, all of United Kingdom

[73] Assignee: Dow Corning Limited, Barry, Wales

[21] Appl. No.: 980,061

[22] Filed: Nov. 23, 1992

[30] Foreign Application Priority Data

Dec. 7, 1991 [GB] United Kingdom ............... 9126049

[51] Int. Cl.$^5$ ............................................. C08G 77/06
[52] U.S. Cl. ..................................... 528/15; 556/479
[58] Field of Search ........................... 528/15; 556/479

[56] References Cited

U.S. PATENT DOCUMENTS 2,823,218 2/1958 Speier et al. ........................ 528/15
4,503,160 3/1985 Williams, Jr. .

FOREIGN PATENT DOCUMENTS 1526324 9/1978 United Kingdom .

Primary Examiner—Melvyn I. Marquis
Attorney, Agent, or Firm—William F. Boley

[57] ABSTRACT

Process for preparing organosilicon compounds having silicon-bonded groups containing olefinic unsaturation by reaction of a silicon compound having SiH groups with a diene having at least 5 carbon atoms and in which the unsaturation is located at the terminal carbon atoms. The process is carried out in the presence of a catalyst which has been prepared by reacting (i) an inorganic solid having surface reactive groups, (ii) an organosilicom compound having a group reactive with the inorganic solid and a group containing nitrogen and/or sulphur and (iii) a platinum compound or complex PtLb in which L is a ligand.

Products have reduced content of isomers resulting from migration of double bond to internal position.

7 Claims, No Drawings

HYDROSILYLATION PROCESS

This invention relates to a process for the preparation of organosilicon materials and which involves the reaction of silicon compounds having ≡SiH groups with dienes.

The reaction of silicon compounds, for example silanes and polysiloxanes, having ≡SiH groups with compounds having olefinic or acetylenic unsaturation is well known. This procedure is often termed hydrosilylation or hydrosilation and is widely employed as a method of synthesis of organosilicon materials. A number of substances are known which are effective in catalysing the hydrosilylation reaction, the most common being the compounds and complexes of the transition metals such as platinum, rhodium and palladium. Specific examples of such catalysts are the platinum and rhodium halides, for example $H_2PtCl_6$, $PtCl_2$, $RhCl_3$, $RhCl_3(SEt_2)_3$ where Et=ethyl, $Rh_2(CO)_4Cl_2$, complexes of platinum chlorides with siloxanes having unsaturated groups and complexes of platinum compounds with olefins.

A variety of organosilicon compounds can be synthesised by means of the hydrosilylation reaction. Organofunctional silanes and siloxanes may be obtained by the addition of ≡SiH in the silane or siloxane to an olefinically-unsaturated compound such as allyl chloride or allyl glycidyl ether. In a similar manner ≡SiH may be reacted with an olefin, for example hexene-1 or decene-1 to produce a silane or siloxane having respectively silicon-bonded hexyl or decyl groups. The hydrosilylation reaction may also be employed to react ≡SiH with dienes to obtain organosilicon compounds having silicon-bonded groups containing olefinic unsaturation. Such unsaturated organo-silicon compounds can be reacted with other organosilicon compounds to obtain useful products such as elastomers and coatings on plastic, paper and other substrates. However, we have found that during the hydrosilylation reaction some isomerisation of the diene occurs resulting in migration of the double bond from a terminal to an internal position in the desired silicon-bonded group. Products having such internal unsaturation exhibit low reactivity with respect to further hydrosilylation to produce elastomers and other products, and thus represent an undesirable component of the reaction product.

We have now surprisingly found that the amount of double bond migration that occurs during the addition of ≡SiH to dienes can be significantly reduced by the use of catalysts comprising certain platinum compounds and complexes chemically bonded to a solid support material. It is disclosed in G. B. 1 526 324 that certain platinum compounds which are chemically bonded to a particulate solid substrate may be employed as catalysts for the hydrosilylation of unsaturated organic compounds, including pentene-1, hexene-2, acetylene and butadiene. However, there is no disclosure or any indication in G.B. 1 526 324 that the use of such catalysts can result in the desirable reduction in internal double-bond migration in the product. G.B. 2 145 701A discloses a hydrosilylation catalyst comprising a hydroxylated oxide of silicon or aluminium having platinum atoms chemically combined through Pt-S linkages. A variety of unsaturated compounds which may be employed in the practice of the hydrosilylation reaction are listed including ethylene, propylene, styrene, vinylacetylene, butadiene and pentadiene. There is, however, no specific disclosure of the use of a diene in which the unsaturation is located only at the terminal carbon atoms or of the advantages associated with the use of such dienes according to the present invention.

Accordingly this invention provides a process for the preparation of an organosilicon compound having a silicon-bonded hydrocarbon group containing olefinic unsaturation which comprises reacting (A) a silicon compound having in the molecule at least one silicon-bonded hydrogen atom, with (B) a diene having at least 5 carbon atoms and wherein the unsaturation is located at the terminal carbon atoms, in the presence of (C) a catalyst which has been prepared by reacting (i) an inorganic solid having surface reactive groups, (ii) an organosilicon compound of the general formula

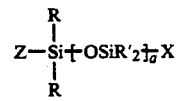

wherein Z represents an atom or group which is reactive with the surface groups in (i), each R represents a chlorine atom, a bromine atom, a monovalent hydrocarbon group having from 1 to 6 carbon atoms, an alkoxy group having from 1 to 6 carbon atoms or an oxime group having less than 14 carbon atoms, each R' represents a monovalent hydrocarbon group having from 1 to 8 inclusive carbon atoms, X represents a monovalent group attached to silicon through a silicon to carbon bond having up to 11 carbon atoms and composed of carbon, hydrogen and optionally oxygen, there also being present in X at least one sulphur or nitrogen atom and a is 0 or an integer of from 1 to 20, and (iii) a platinum compound or complex $PtL_b$ wherein each L represents a ligand at least one of which is displaceable by amino or mercapto and b is a number such that the free valencies of Pt are satisfied.

As the silicon compound (A) there may be employed in the process of this invention any monomeric, oligomeric or polymeric compound having at least one ≡SiH group. Such compounds and their use in hydrosilylation reactions are well documented in the art and include silanes, linear polysiloxanes, branched polysiloxanes and cyclic siloxanes. The nature of the silicon-bonded substituents present in addition to the hydrogen atoms is not critical but normally such substituents will be selected from monovalent hydrocarbon groups having from 1 to 10 carbon atoms and free of aliphatic unsaturation, halogen e.g. chlorine atoms and alkoxy groups having less than about 8 carbon atoms. Examples of such compounds are $C_6H_5SiHCl_2$, $HSi(OCH_3)_3$, $HSiCl_3$, $CH_3HSi(OC_2H_5)_2$, $(CH_3)_2HSiCl$, methylhydrogen polysiloxanes and copolymers of methylhydrogensiloxane units with one or more other siloxane units for example dimethylsiloxane, trimethylsiloxane and dimethylhydrogensiloxane units. The process of the invention is, however, of particular interest in connection with the reactions of chloroilanes, for example $CH_3HSiCl_2$ and $HSiCl_3$ which appear to show the greatest reduction in internal bond migration.

Reactant (B) may be any diene having at least 5 carbon atoms and wherein the unsaturation (double bonds) are located at the terminal carbon atoms, for example 1,4-pentadiene, 1,5-hexadiene, 1,9-decadiene and 1,13-tetradecadiene. Preferred dienes are those having from 6 to 14 carbon atoms.

The catalyst (C) is prepared by the reaction of the inorganic solid (i) with the organosilicon compound (ii) and the platinum complex (iii) to provide a product which is believed to comprise platinum chemically bonded to the substrate through the group

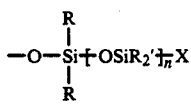

the platinum being coordinately linked to one or more nitrogen or sulphur atoms in X which may be in the same or in different linking groups. The reaction may be performed by mixing the reactants in any sequence, for example by mixing (i), (ii) and (iii) employing elevated temperatures and catalysts as necessary. Alternatively the platinum complex (iii) may first be reacted with the organosilicon compound (ii) and the product then reacted with the solid (i). A more convenient and preferred procedure for the preparation of the catalyst (C) is that described in G.B. 1 526 324 wherein as a first step the organosilicon compound (ii) is reacted with the solid (i) and the product then reacted as a second step with the platinum compound or complex (iii).

The reaction between the organosilicon compound (ii), with or without the presence of the coordinated Pt, and the solid substrate (i) is conveniently carried out in the presence of an inert solvent, for example toluene, xylene, pentane or heptane. When the organosilicon compound is water soluble we prefer to carry out the reaction in an aqueous medium. Although in some cases reaction will occur at normal ambient temperature it is preferred to accelerate the reaction by the use of elevated temperatures, usually from about 80° C. to 150° C. If desired catalysts may be employed to expedite the reaction, examples of suitable catalysts being sodium ethoxide, lead octoate, dibutyltin diacetate and other silanol condensation catalysts.

Reaction between the organosilicon compound (ii) or the substrate-bound organosilicon compound with the platinum complex (iii) will normally occur at ambient temperatures, that is from about 15° to 25° C. However, higher temperatures may be used if desired. The reaction is preferably carried out in the presence of solvent, most preferably a polar solvent e.g. methanol, ethanol, dioxane and/or water. The platinum compound or complex is preferably reacted in a proportion which provides in the catalyst from 5 to 200 atoms, most preferably from 30 to 150 atoms, of nitrogen or sulphur per atom of platinum.

In the general formula of the organosilicon compound (ii) the substituent Z may be any atom or group which is reactive with the hydroxyl groups on the solid, and may be for example chlorine, bromine, alkoxy such as methoxy, ethoxy, propoxy, butoxy, methoxyethoxy, hydroxyl and oxime e g. $-ON=C(C_2H_5)_2$ and $-ON=C(C_6H_5)_2$ Each of the R substituents may be of the same type as those exemplified for Z but may also be selected from alkyl, aryl, aralkyl, alkaryl and halogenated alkyl. Preferably Z represents an alkoxy group having from 1 to 4 carbon atoms e.g. methoxy or ethoxy and R represents methyl, phenyl or an alkoxy group having from 1 to 4 carbon atoms.

Each substituent R', when present, may be for example methyl, propyl, hexyl or phenyl. The group X is a monovalent group attached to silicon via a silicon to carbon linkage and having therein at least one sulphur or nitrogen atom. It is preferably composed of carbon and hydrogen, in addition to the nitrogen and/or sulphur, but may contain oxygen in the form of ether linkages. Specific examples of X groups are $-(CH_2)_3SH$, $-(CH_2)_4SH$, $-CH_2CH(CH_3)CH_2S$ ), $(C_6H_4)$, $(CH_2)_3NH_2$, $-(CH_2)_4NHCH_3$, $-CH_2CH(CH_3)CH_2$, $N(C_3H_7)_2$, $-(CH_2)_3NHCH_2CH_2NH_2$ and $-(CH_2)_4NH(CH_2)_4NH_2$. Preferably X is $-(CH2)3NHCH2CH2NH2$ and $-(CH2)4NH(CH$ Preferably X is a nitrogen-containing group, for example $-(CH_2)_3NH_2$, $-(CH_2)_3NHCH_2CH_2NH_2$ or $-CH_2CH(CH_3)CH_2NHCH_2CH_2NH_2$. The ligand or ligands L may be for example alkyl e.g. methyl, butyl or hexyl, phenyl, $-CO$, halide e.g. chlorine, H, acetylacetonate, amino or olefin e.g. $CH_2=CH_2$. Examples of the operative platinum compounds or complexes (iii) are $PtCl_2$, $H_2PtCl_6$, $Na_2PtCl_4.4H_2O$, $K[Pt(CH_2=CH_2)Cl_3]H_2O$, $Pt_2(CH_2=CH_2)_2Cl_4$, $Cl_2Pt(Et_2S)_2$ in which Et=ethyl, $[PtCl_2P(C_6H_5)_3]_2$, $PtCl_2[P(C_6H_5)_3]_2$ and $PtBr_2(NH_3)_2$.

The solid to which the groups (i) are attached is preferably particulate and inorganic and must be susceptible to the chemical attachment of the groups (i). Such solids will in general be those which prior to the attachment of the organo-silicon linking group have surface groups, usually hydroxyl, capable of reacting with organo-silicon compounds to provide the required surface-bonded sulphur- and/or nitrogen-containing groups. Particularly preferred as the particulate solids are the silicas e.g. quartz, precipitated silicas and silica gel. Other solids, for example zeolitic molecular sieve, kaolin, alumina and titania can, however, be employed. When the solid is in particulate form it preferably has a particle size within the range from 5 to 100 mesh British Standard Test Sieve (BS 410:1962) whereby its separation from the reaction product of the diene and silicon-hydrogen compound may be more readily accomplished.

Reaction between the silicon-hydrogen compound (A) and the diene (B) may be carried out employing any conventional process techniques. For example it may be performed at atmospheric, sub-atmospheric or super-atmospheric pressures, in the presence or absence of solvents and at temperatures from below 20° C. to above 160° C. Normally it is preferred to expedite the reaction by employing temperatures in the range from about 80° C. to about 180° C. and, if desired, super-atmospheric pressure. In order to minimise the reaction of the silicon-hydrogen compound with both of the unsaturated groups in the diene, the diene is preferably employed in an excess of at least twice the stoichiometric amount. The catalyst (C) may be readily recovered from the reaction mixture by decantation or filtration. After recovery the catalyst may be recycled. However, because of their heterogeneous nature the catalysts (C) are particularly suitable for use on a continuous, rather than a batch, basis. The process of this invention may therefore be performed by passing the diene (B) and silicon-hydrogen compound (A) over or through a bed of the catalyst (C) employing reaction conditions, for example temperature and pressure, to achieve the desired reaction times and products.

The products obtained by the process of this invention are silanes and siloxanes which have therein at least one silicon-bonded hydrocarbon group containing olefinic unsaturation. By employing the catalyst (C) it has been found possible to obtain a product wherein the proportion of non-terminal olefinic unsaturation is significantly reduced compared with processes employing more conventional platinum catalysts. The products of the process of this invention may be employed in the preparation of organosilicon compositions, for example elastomers and coating compositions where they may be cured by hydrosilylation or other reactions.

The following Examples in which Me represents methyl and Et represents ethyl illustrate the invention.

EXAMPLE 1

$(EtO)_3Si(CH_2)_3NH_2$ (90 g) dissolved in water (2500 g) was added to silica gel (Grace ID 112) (300 g) and the mixture agitated at normal ambient temperature for about 16 hours. The silica gel containing 1.43% N by weight was recovered and dried. This product (100 g) was then mixed with $Na_2PtCl_4.4H_2O$ (4.71 g) dissolved in water (400 ml) and methanol (200 ml). The solid was recovered and dried to provide a particulate catalyst having 0.49% by weight of platinum and a mole ratio of N:Pt of 40:1.

1,5-hexadiene (98.4 g), $HSiMeCl_2$ (46.0 g) and 1.63 g of the catalyst prepared as described above were mixed in a flask and heated to reflux temperature for 4 hours. After distillation to remove excess 1,5-hexadiene there was obtained 60.7 g of a mixture of 5-hexenyl(methyl)-dichlorosilane and $Cl_2MeSi(CH_2)_6SiMeCl_2$. The hexenyl silane was found to be less than 1% isomerised to the internally unsaturated isomer. When the reaction was repeated employing a solution of $H_2PtCl_6 6H_2O$ in isopropyl alcohol in an amount to provide the same weight of Pt the hexenyl silane was found to contain 33% of internal bond isomer.

The catalyst was recycled and reused a further six times to react a total of 688.8 g of 1,5-hexadiene with 322 g of $HMeSiCl_2$.

EXAMPLE 2

A glass tube having an internal diameter of 1.5 cm and of length 41 cm was packed with 18.5 g of the catalyst prepared as described in Example 1. A mixture of 6.72 kg of $HSiMeCl_2$ and 15.1 kg of 1,5-hexadiene was then passed over the catalyst during a period of 234 hours. Analysis of the product issuing from the tube showed that substantially complete reaction had taken place and the resulting hexenyl(methyl)dichlorosilane product was less than 1% isomerised.

EXAMPLE 3

$(MeO)_3SiCH_2CH_2SCH_2CH_3$ (45 g) dissolved in toluene (1000 g) was added to silica gel (150 g, Grace ID 112) and the mixture heated at 95° C. for 12 hours. After 3 hours heating n-hexylamine (0.5 ml) (as catalyst) was added to the reaction mixture. The silica gel was then recovered, extracted with hot toluene and dried to give a product containing 3.18% by weight of sulphur. This product (100 g) was then mixed with water (300 ml), methanol (200 ml) and a solution of $Na_2PtCl_4.4H_2O$ (1.13 g) in water (100 ml) and the resulting mixture was agitated at room temperature for 24 hours. The solid was recovered, washed with methanol (5×400 ml), ether (3×400 ml) and dried to provide a particulate catalyst having 0.51% by weight of platinum and a mole ratio of S:Pt of 38:1.

1,5-hexadiene (49.2 g, 0.6 mol), methyldichlorosilane (23.0 g, 0.2 mol) and 0.38 g of the above catalyst ($10^{-5}$ mol Pt) were charged to a flask and heated to reflux. The reaction proceeded smoothly to completion during which time the reflux temperature rose from 53° to 72° C. The products were then decanted from the catalyst and further 1,5-hexadiene (49.2 g) and methyldichlorosilane (23.0 g) added to the flask and the reaction repeated. The catalyst was similarly recycled a further two times. Gas-liquid chromatographic analysis of the resulting product gave the peak area percentages shown in the table, times for complete reaction are also given.

| Cycle | 1 | 2 | 3 | 4 |
|---|---|---|---|---|
| Reaction time/m | 473 | 390 | 472 | 869 |
| 1,5-hexadiene | 57.1 | 57.4 | 59.3 | 70.9 |
| 1-(methyldichloro-silyl)-5-hexene | 39.6 | 41.0 | 38.8 | 28.0 |
| 1,6-bis(methyldi-chlorosilyl)hexane | 2.6 | 1.4 | 1.6 | — |

Proton N.M.R. analysis of the 1-(methyldichlorosilyl)-5-hexene showed that 2.8% of the terminal double bonds had migrated to an internal position.

EXAMPLE 4

$(MeO)_3SiCH_2CH_2CH_2NH_2$ (15 g) dissolved in water (3000 g) was added to silica gel (600 g, Grace ID 113) and the mixture agitated at ambient temperature for 24 hours. The silica gel was then recovered, extracted with hot toluene and dried to give a product containing 0.1% by weight of nitrogen. This product (50 g) was then mixed with water (150 ml) and methanol (100 ml) and a solution of $Na_2PtCl_4.4H_2O$ (0.0325 g) in water (50 ml), the resulting mixture was agitated at room temperature for 24 hours. The solid was recovered, washed with methanol (5×200 ml), ether (3×200 ml) and dried to provide a particulate catalyst having 0.011% by weight of platinum and a ratio of N:Pt of 126:1.

1,5-hexadiene (49.2 g, 0.6mol), methyldichlorosilane (23.0 g, 0.2mol) and 8.8 g of the above catalyst (5×10 mol Pt) were charged to a flask and heated to reflux. The reaction proceeded smoothly to completion during which time the reflux temperature rose from 53° C. to 72° C. The products were then decanted from the catalyst and further 1,5-hexadiene (49 2 g) and methyldichlorosilane (23.0 g) added to the flask and the reaction repeated. The catalyst was similarly recycled a further two times. Gas-liquid chromatographic analysis of the resulting product gave the peak area percentages shown in the table, times for complete reaction are also given.

| Cycle | 1 | 2 | 3 | 4 |
|---|---|---|---|---|
| Reaction time/m | 335 | 282 | 289 | 216 |
| %1,5-hexadiene | 56.2 | 65.1 | 64.8 | 66.1 |
| %1-(methyldichloro-silyl)-5-hexene | 39.0 | 34.7 | 34.9 | 33.6 |
| %1,6-bis(methyldi-chlorosilyl)hexane | 2.9 | 0.1 | 0.2 | 0.1 |

Proton N.M.R. analysis of the 1-(methyldichlorosilyl)-5-hexene showed that 1.1% of the terminal double bonds had migrated to an internal position.

EXAMPLE 5

1,13-tetradecadiene (155.2 g, 0.8mol), methyldichlorosilane (23.0 g, 0.2mol) and a hydrosilylation catalyst 0.40 g, $10^{-5}$ mol Pt, prepared as described in Example 1) were charged to a reaction vessel. The reagents were heated to 66° C. which increased to 90° C. over a period of 90 minutes, the reaction mixture was then maintained at this temperature for a further 150 minutes. Gas-liquid chromatographic analysis of the resulting product gave the following peak area percentages:

| | |
|---|---|
| 1,13-tetradecadiene | 72.9% |
| 1-(methyldichlorosilyl)-13-tetradecene | 17.7% |
| 1,14-bis(methyldichlorosilyl)tetradecane | 2.4% |

Proton N.M.R. analysis of the 1-(methyldichlorosilyl)-13- tetradecene showed that 2.9% of the terminal double bonds had migrated to an internal position.

EXAMPLE 6

1,5-hexadiene (246 g, 3.0 mol), 1,1,3,3-tetramethyldisiloxane (105 g, 0.75mol) and 1.88 g of a catalyst ($5 \times 10^{-5}$ mol Pt prepared as in Example I) were charged to a flask and heated to reflux. The reaction proceeded smoothly to completion during which time the reflux temperature rose from 58° C. to 72° C. The products were then decanted from the catalyst and further 1,5-hexadiene (246 g) and 1,1,3,3-tetramethyldisiloxane (105 g) added to the flask and the reaction repeated. Gas-liquid chromatographic analysis of the resulting product gave the peak area percentages shown in the table, times for complete reaction are also given.

| Cycle | 1 | 2 |
|---|---|---|
| Reaction time/h | 3.5 | 3.3 |
| 1,5-hexadiene | 49.9 | 50.2 |
| 1,3-bis(5-hexenyl)-1,1,3,3-tetramethyldisiloxane | 31.7 | 30.6 |
| Higher molecular weight products | 17.1 | 17.2 |

Proton N.M.R. analysis of the 1,3-bis(5-hexenyl)-1,-1,3,3-tetramethyldisiloxane showed that 1.6% of the double bonds had migrated to an internal position.

EXAMPLE 7

The procedure and catalyst described in Example 1 were employed to react $HSiCl_3$ (27.1 g) with 1,5-hexadiene (49.2 g). The hexenyl silane product contained only 1.6% of the internal bond isomer. When the reaction was repeated employing a solution of $H_2PtCl_6 6H_2O$ in isopropyl alcohol as catalyst the percentage of isomer was 7.8.

That which is claimed is:

1. A process for the preparation of an organosilicon compound having a silicon-bonded hydrocarbon group containing olefinic unsaturation which comprises reacting (A) a silicon compound having in the molecule at least one silicon-bonded hydrogen atom, with (B) a diene having at least 5 carbon atoms and wherein the unsaturation is located at the terminal carbon atoms, in the presence of (C) a catalyst which has been prepared by reacting (i) an inorganic solid having surface reactive groups, (ii) an organosilicon compound of the general formula

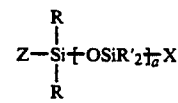

wherein Z represents an atom or group which is reactive with the surface groups in (i), each R represents a chlorine atom, a bromine atom, a monovalent hydrocarbon group having from 1 to 6 carbon atoms, an alkoxy group having from 1 to 6 carbon atoms or an oxime group having less than 14 carbon atoms, each R' represents a monovalent hydrocarbon group having from 1 to 8 inclusive carbon atoms, X represents a monovalent group attached to silicon through a silicon to carbon bond having up to 11 carbon atoms and composed of carbon, hydrogen and optionally oxygen, there also being present in X at least one sulphur or nitrogen atom and a is O or an integer of from 1 to 20, and (iii) a platinum compound or complex $PtL_b$ wherein each L represents a ligand at least one of which is displaceable by amino or mercapto and b is a number such that the free valencies of Pt are satisfied.

2. A process as claimed in claim 1 wherein the inorganic solid (i) is a silica.

3. A process as claimed in claim 1 wherein the diene (B) has from 6 to 4 carbon atoms.

4. A process as claimed in claim 1 wherein the ratio of N or S atoms to Pt atoms in the catalyst (C) is from 30:1 to 150:1.

5. A process as claimed in claim 1 wherein X is a nitrogen-containing group.

6. A process as claimed in claim 1 wherein the organosilicon compound (A) is selected from a group consisting of $CH_3HSiCl_2$ and $HSiCl_3$.

7. A process as claimed in claim 1 wherein the reactants (A) and (B) are passed over or through a bed of the catalyst (C).

* * * * *